United States Patent [19]

Boyer

[11] 4,455,689
[45] Jun. 26, 1984

[54] GOGGLE WITH TEAR OFF TRANSPARENCIES

[76] Inventor: Wayne E. Boyer, 12118 Poway Rd., Poway, Calif. 92064

[21] Appl. No.: 423,622

[22] Filed: Sep. 27, 1982

[51] Int. Cl.³ .............................................. A61F 9/02
[52] U.S. Cl. ...................................................... 2/434
[58] Field of Search ................... 2/434, 439, 440, 441, 2/443, 447, 452, 429, 426, 436, 438, 174

[56] References Cited

U.S. PATENT DOCUMENTS

| | | | |
|---|---|---|---|
| 1,308,477 | 7/1919 | Blanchard | 2/441 |
| 3,945,044 | 3/1976 | McGee et al. | 2/434 X |
| 4,076,373 | 2/1978 | Moretti | 2/434 X |
| 4,138,746 | 2/1979 | Bergmann | 2/434 X |

Primary Examiner—Peter P. Nerbun
Attorney, Agent, or Firm—Brown & Martin

[57] ABSTRACT

A specially configured and dimensioned bracket is inserted through the strap slot at one side end of a goggles frame. A plurality of transparencies are installed over the lens, one at a time. Peripheral tabs on the lens shaped portion of each transparency are inserted between the lens and the goggles frame. A retaining pin extending from the bracket is forced through a small hole formed in the inner end of an arm portion which extends from one end of the lens portion of the transparency. The arm portion of the transparency is folded back on itself so that the retaining pin extends through a large hole in the outer end of the arm portion. The arm portion of the outermost transparency is not folded but is left free to be grasped with one hand so that the transparency can be torn away from the goggles frame when soiled, thereby enhancing a racer's vision. When this is done, the arm portion of the outermost transparency just uncovered unfolds but remains attached to the retaining pin.

14 Claims, 4 Drawing Figures

GOGGLE WITH TEAR OFF TRANSPARENCIES

BACKGROUND OF THE INVENTION

The present invention relates to protective eye wear, and more particularly, to goggles having transparencies which cover the lens and are torn away during a race instead of cleaning the lens.

Motorcross racers typically drive their motocycles at high speeds across rough terrain. Along with various other equipment for protecting the body, these racers typically wear goggles. During a race, dirt and mud build up on the lens of goggles. This substantially impairs the racer's vision and if not corrected, can cause an accident and serious injury. However, because the racer is required to keep both of his hands on the respective handlebar grips of the motorcycle to maintain control, it is extremely difficult to effectively wipe the lens clean during a race. The amount of time that one of the racer's hands would have to be off the handlebar grip could result in a loss of control and an accident. If the racer slows down sufficiently to safely clean the lens, then it is likely that he will be passed by other racers and will loose the race.

One solution to this problem has been provided by a commercially available goggle in which a webbing of clean transparent material is fed across the lens of the goggle between rollers mounted at the opposite side edges of the goggles. When the segment of transparent webbing overlying the lens becomes too dirty, the racer pulls on a cord and mechanisms cause a clean segment of the transparent webbing to be pulled across the lens. However, these goggles require mechanical feed mechanisms which are subject to failure and the complexity of this solution makes it generally one that has not yet received wide spread receptance.

Another solution to this problem of dirty goggles that has received widespread acceptance is the use of tear off transparencies. These comprise individual, thin pieces of transparent plastic material having a general shape of the goggle lens. The transparencies normally have tabs around their peripheral edges. A plurality of these transparencies may be overlaid on the goggle lens, and their tabs inserted between the lens and the flexible lens frame to hold them into position. Generally, these transparencies have an extended arm portion at one side thereof which extends past the side edge of the goggle. These arm portions may extend at different angles in the general plane of the lens. During a race, dirt and mud builds up on the outermost transparency. When the vision is sufficiently obscured, the motorcross racer can reach up with one hand and tear away one of the transparencies with one quick motion. The dirty transparency then falls to the ground and the racer has a clear view through the lens and remaining unsoiled transparencies. A principal drawback in the foregoing arrangement is that the transparencies are held to the lens only by the tabs. Furthermore, the number of transparencies that can be used is limited to a small number, for example three, since there is only a limited amount of angle through which arm portions of the transparencies can extend, and not yet overlap.

Recently, a new type of goggles equipped with tear off transparencies has been marketed under the trademark OAKLEY. In this goggle, an element with a small round head projects outwardly from the lens adjacent one side edge thereof. The transparencies are all identical, each having an arm portion which extends from the left side edge thereof viewed from the racer's standpoint. The arm portions have a large circular hole adjacent their outer end. Each of these transparencies further has insertion tabs around the peripheral side edges thereof and a small hole which tightly fits over the rounded portion of the element which projects from the lens. When a plurality of these transparencies are inserted over the lens of the goggles, they are put in place one at a time.

The transparencies used with the OAKLEY goggles are inserted as follows. The tabs of a first transparency are inserted between the lens and the flexible lens frame. Then the portion of the transparency having the small hole in it is forced over the rounded end of the projecting element. The arm portion of the first transparency is then curled back on itself, away from the goggles. The outer ring of the arm portion is hooked around the projecting element. The arm portion of the first transparency is held in its folded configuration with its ring portion engaged with the element until the next transparency is put in place and the projecting element is forced through its small hold. This serves to retain the arm portion of the first transparency immediately below in its folded state. Each succeeding transparency is similarly installed on the goggle. The arm portion of the last transparency is not folded but is left hanging out, extending beyond the folded arm portions of the transparencies below.

During a race, a motorcycle racer wearing the OAKLEY goggles can easily grasp the arm portion of the outermost transparency and pull this transparency free of the projecting element and from the lens with one quick motion. When this is done, the arm portion of the transparency immediately beneath unfolds, and is ready for grasping by the racer when it time once again to clean his goggles.

While the arrangement utilized in the OAKLEY goggles has a number of advantages, its principal disadvantage is that a special lens must be fashioned with a projecting element which extends therethrough adjacent one side edge of the lens. Furthermore, the projecting element in the lens tends to obstruct the view since the projecting element is opaque. The folded arm portions of the multiple transparencies tend to be clumped over the side edge portion of the lens. It would be desirable to provide a means of retrofitting existing goggles so that they could use the folding type of transparencies without having to replace their lens.

SUMMARY OF THE INVENTION

It is therefore the primary object of the present invention to provide goggles with an improved system for keeping them clean.

Another object of the present invention is to provide an improved system of mounting tear off transparencies to racing goggles.

Still another object of the present invention is to Provide a special bracket for retrofitting commercial goggles so that they can be used with the folding type of tear off transparencies.

Accordingly, a specially configured and dimensioned bracket is inserted through the strap slot at one side end of a goggles frame. A plurality of transparencies are installed over the lens, one at a time. Peripheral tabs on the lens shaped portion of each transparency are inserted between the lens and the goggles frame. A retaining pin extending from the bracket is forced through a small hole formed in the inner end of an arm portion which extends from one end of the lens portion of the transparency. The arm portion of the transparency is folded back on itself so that the retaining pin extends through a large hole in the outer end of the arm portion. The arm portion of the outermost transparency is not folded but is left free to be grasped with one hand so that the transparency can be torn away from the goggles frame when soiled, thereby enhancing a racer's vision. When this is done, the arm portion of the outermost transparency just uncovered unfolds but remains attached to the retaining pin.

DESCRIPTION OF THE PREFERRED EMBODIMENT

Figure 1:
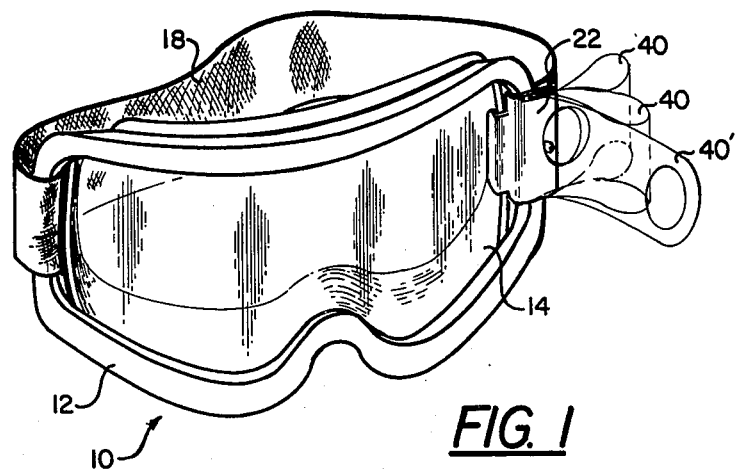
FIG. 1 is a perspective view of a pair of commercially available goggles fitted with a preferred embodiment of my invention.
Figure 3:
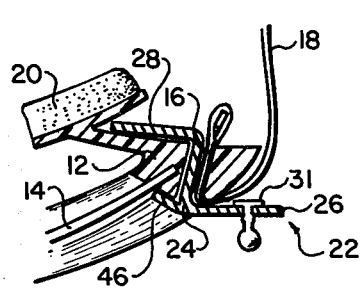
FIG. 3 is a sectional view taken along line 3—3 of FIG. 2.

Referring to FIG. 1, my invention is designed to be utilized with a conventional pair of goggles 10 such as those sold under the trademark CARRERA by Carrera International Corporation, P.O. Box 2, Norwood, N.J., 07648. These goggles have a flexible frame 12 which surrounds the peripheral portions of a lens 14 as best seen in FIG. 3. The goggles have vertical slots 16 formed in the side portions of the frame 12 through which extend the ends of a strap 18. The inner facing edges of the goggles frame 12 may be lined with foam rubber 20 (FIG. 3).

Figure 2:
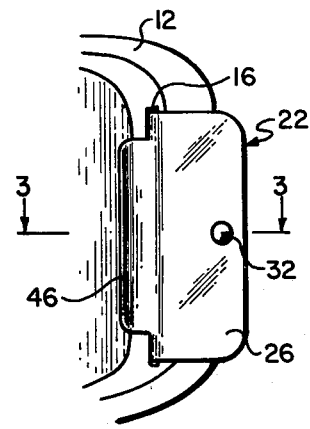
FIG. 2 is an enlarged view of the left hand edge portion of the goggles of FIG. 1 showing the special bracket of my invention.

According to my invention, a specially configured bracket 22 (FIGS. 1, 2 and 3) is inserted into the left one of the slots 16 in the frame. The bracket 22 has a central planar portion 24 and two reversely bent, parallel extending planar portions 26 and 28 which extend from the side edges of the central planar portion.

The vertical dimension of the planar portions 24 and 26 is slightly smaller than the length of the slot 16 to enable these portions to be inserted through the slot. The squeezing action of the portion of the frame defining the slot helps to hold the bracket in position. The central planar portion 24 extends at a slight angle from the perpendicular with respect to the outer planar portions 26 and 28. The width of the central planar section 24 is slightly less than the depth of the slot 16. Thus, the end of the goggles frame is slightly squeezed between the outer planar portions 26 and 28 to further hold the bracket 22 visibly in position. The outer planar portion 26 has a retaining pin 30 inserted therethrough. The retaining pin has an outwardly extending portion with an enlarged, rounded head 32 on the outer end thereof.

The retaining pin 30 has a flat base 31. The shaft of the retaining pin extends through a hole in the planar portion 26 of the bracket. The flat base 31 thus abuts against the rear side of the planar portion 26. A slightly flared portion of the retaining pin immediately below the rounded portion 32 serves to rigidly hold the retaining pin in position as illustrated in FIG. 3.

Figure 4:
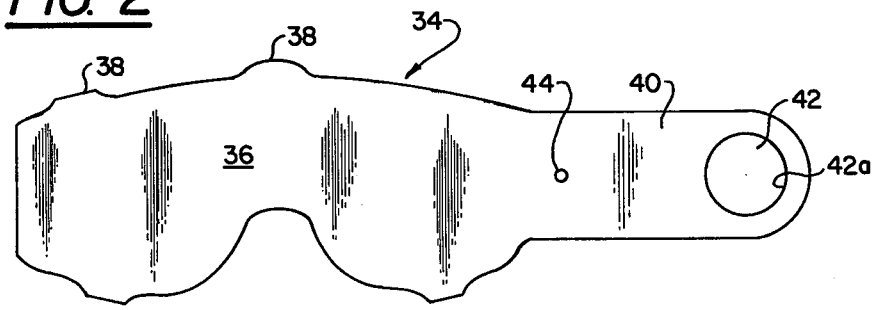
FIG. 4 is a plan view of the transparency utilized with my invention.

A plurality of tear off transparencies 34 (FIG. 4) may be installed on the goggles as illustrated in FIG. 1. Each of the transparencies 34 (FIG. 4) has a main lens shaped portion 36 adapted to cover the lens 14 of the goggles. The lens portion 36 has an outline configured so that peripheral tabs 38 formed thereon can be inserted between the goggle lens 14 and the flexible goggle frame 12. Each transparency 34 also has an arm portion 40 which extends from the left side thereof. The arm portion has a large circular hole 42 formed in the outer end thereof and a small hole 44 formed in the inner end thereof. A small hole 44 is positioned and dimensioned so that when the transparency 34 is inserted in place over the lens of the goggles, the retaining pin 30 on the bracket 22 may be forced therethrough. Thus, the diameter of the small hole 44 is slightly smaller than the diameter of the round head 32 of the retaining pin. Thereafter, the arm portion 40 of the transparency is folded back on itself, away from the goggles so that the retaining pin extends through the large hole 42 and contacts the outer edge 42a thereof as illustrated in FIG. 1.

Another identical transparency may then be inserted over the previous transparency and the retaining pin is inserted through its small hole 44. Thus, this serves to keep the arm portion 40 of the transparency immediately beneath folded as illustrated in FIG. 1. The desired number of transparencies, for example ten, may be repeatedly installed in this manner. When the last transparency is inserted into the goggles, the retaining pin is pushed through the small hole 44 therein, however the arm portion of the last transparency is not folded over but is allowed to extend outwardly as illustrated in FIG. 1. The arm portion of the last transparency therein is denoted 40'.

The bracket 22 further includes an inwardly angled flange 46 (FIGS. 2 and 3) which contacts the lens 14 of the goggles to thereby aid in holding the bracket rigidly in position. The flange 46 has a height in FIG. 2 which is slightly smaller than the height of the planar portion 26 of the bracket. As illustrated in FIG. 3, the joints between the side edges of the central planar portion 24 and the outer planar portions 26 and 28 are curved. In addition, the corners of the planar portions and of the flange are curved. This enables the bracket to be forced through the slot 16 more easily and reduces the risk of damaging the goggle frame.

The bracket may be made of a single piece of extruded aluminum, and the retaining pin may be made of plastic. Alternatively, the entire bracket and retaining pin could be a single molded piece of plastic.

Having described a preferred embodiment of my invention, it should be apparent to those skilled in the art that my invention may be modified in both arrangement and detail. Therefore, the protection afforded my invention should be limited only in accordance with the scope of the following claims.

I claim:

1. An apparatus for removably mounting a plurality of tear off transparencies over the outer side of the lens of goggles having a deformable surrounding frame with a vertical slot extending through one side edge thereof, each transparency having an arm portion which extends from one end thereof, the arm portion having a hole formed therein, comprising:

a bracket having a portion insertable in the slot in the goggle frame and means for retaining the insertable portion in the slot; and a retaining pin extending outwardly from the bracket and having an enlarged head slightly larger than the hole in the arm portion of the transparency.

2. An apparatus according to claim 1 wherein the retaining means comprises at least one arm portion which extends angularly from the insertable portion and engages the side edge of the goggle frame.

3. An apparatus according to claim 1 wherein the bracket is dimensioned such that the squeezing action of the portion of the goggle frame defining slot aids in holding the bracket in position.

4. An apparatus according to claim 1 wherein the bracket is configured to slightly squeeze the portion of the goggle frame defining the slot to hold the bracket in position.

5. An apparatus according to claim 1 wherein the retaining means comprises a pair of substantially reversely bent arms extending from a pair of opposite side edges of the insertable portion.

6. An apparatus for removably mounting a plurality of tear off transparencies over the outer side of the lens of goggles having a surrounding frame with a vertical slot extending through one side edge thereof, each transparency having an arm portion which extends from one end thereof, the arm portion having a hole formed in its outer end and a hole formed in its inner end, comprising:

a bracket adapted to be inserted through the slot in the goggle's frame; and a retaining pin extending outwardly from the bracket and having an enlarged head slightly larger than the inner hole in the arm portion of the transparency;

wherein the bracket includes a central planar portion, and a pair of second portions adjoined along opposite side edges of the central planar portion and extending in opposite directions.

7. An apparatus according to claim 6 wherein the bracket further comprises a flange extending from the outer side edge of the central planar portion for contacting the lens of the goggles.

8. An apparatus according to claim 6 wherein the second planar portions extend generally perpendicular to the central planar portion.

9. An apparatus according to claim 6 wherein the enlarged outer end of the retaining pin is rounded.

10. An apparatus according to claim 7 wherein the vertical height of the flange is less than the vertical height of the second planar portions.

11. An apparatus according to claim 6 wherein the second planar portions extend generally parallel and the central planar portion extends therebetween at an angle slightly offset from perpendicular with respect to the second planar portions.

12. An apparatus according to claim 7 wherein the edges of the planar portions are curved.

13. An apparatus according to claim 6 wherein the joints between the planar portions are curved to facilitate insertion of the bracket through the slot in the frame of the goggles.

14. An apparatus according to claim 7 wherein the flange extends inwardly at an angle to the lens with respect to the outermost one of the second planar portions.

* * * * *